United States Patent
Takacs et al.

(10) Patent No.: US 9,375,450 B2
(45) Date of Patent: Jun. 28, 2016

(54) VAGINAL TISSUE REJUVENATION COMPOSITIONS AND METHODS

(75) Inventors: Peter Takacs, Miami Beach, FL (US); Keith A. Candiotti, Miami Beach, FL (US); Carlos A. Medina, Miami Lakes, FL (US)

(73) Assignee: Peter Takacs, Norfolk, VA (US)

( * ) Notice: Subject to any disclaimer, the term of this patent is extended or adjusted under 35 U.S.C. 154(b) by 0 days.

(21) Appl. No.: 14/239,774

(22) PCT Filed: Jul. 10, 2012

(86) PCT No.: PCT/US2012/046072
§ 371 (c)(1),
(2), (4) Date: Feb. 19, 2014

(87) PCT Pub. No.: WO2013/012614
PCT Pub. Date: Jan. 24, 2013

(65) Prior Publication Data
US 2014/0220155 A1    Aug. 7, 2014

Related U.S. Application Data

(60) Provisional application No. 61/510,333, filed on Jul. 21, 2011.

(51) Int. Cl.
| | | |
|---|---|---|
| A61K 33/30 | (2006.01) |
| A61K 31/426 | (2006.01) |
| A61F 6/08 | (2006.01) |
| A61K 31/192 | (2006.01) |
| A61K 31/20 | (2006.01) |

(52) U.S. Cl.
CPC . *A61K 33/30* (2013.01); *A61F 6/08* (2013.01); *A61K 31/192* (2013.01); *A61K 31/20* (2013.01); *A61K 31/426* (2013.01)

(58) Field of Classification Search
CPC ..... A61K 33/30; A61K 31/192; A61K 31/20; A61K 31/426
USPC .................. 424/401, 434, 641, 642
See application file for complete search history.

(56) References Cited

U.S. PATENT DOCUMENTS

| | | | |
|---|---|---|---|
| 4,372,296 A | 2/1983 | Fahim | |
| 4,711,780 A | 12/1987 | Fahim et al. | |
| 8,148,389 B2 | 4/2012 | Nakamura et al. | |
| 2005/0054608 A1 | 3/2005 | Linge et al. | |
| 2005/0095232 A1* | 5/2005 | Volkmann | 424/93.45 |
| 2006/0088615 A1* | 4/2006 | Seiberg et al. | 424/769 |
| 2010/0278784 A1 | 11/2010 | Pojasek et al. | |
| 2011/0002966 A1* | 1/2011 | Lovett et al. | 424/400 |
| 2011/0021422 A1 | 1/2011 | Tennenbaum et al. | |
| 2011/0195993 A1 | 8/2011 | Masson et al. | |

FOREIGN PATENT DOCUMENTS

| | | |
|---|---|---|
| WO | WO-2010121081 A1 | 10/2010 |
| ZA | 200308879 A | 7/2004 |

OTHER PUBLICATIONS

International Search Report and the Written Opinion of the ISA mailed on Sep. 12, 2012 in PCT Application No. PCT/US2012/46072. (13 pages).
Jackson et al., "The Effects of Oestradiol on Vaginal Collagen in Postmenopausal Women with Stress Urinary Incontinence," Neurology and Urodynamics, vol. 15, Aug. 27, 1998 (pp. 327-328) XP008049149.
Partial Supplementary European Search Report of the European Patent Office mailed on Jan. 7, 2015 in European Patent Application No. 12814521.6 (8 pgs.).
Takacs et al., "Effects of PPAR-Delta Agonist and Zinc on Vaginal Smooth Muscle Cells Collagen and Tropoelastin Production," International Urogynecology Journal, vol. 23, May 11, 2012 (pp. 1775-1779) XP035149494.

* cited by examiner

*Primary Examiner* — Gina Justice
(74) *Attorney, Agent, or Firm* — Grimes & Yvon LLP

(57) ABSTRACT

A method of stimulating elastin and/or collagen production in the tissues of the vagina, comprising the steps of providing a composition including at least one of a water soluble zinc salt such as zinc sulfate and a peroxisome proliferator-activated receptor beta/delta (PPAR β/δ) agonist, and administering the composition to the tissue of the vagina. Compositions for stimulating 5 elastin and/or collagen production in the tissues of the vagina are also disclosed.

12 Claims, 20 Drawing Sheets

VAGINAL TISSUE REJUVENATION COMPOSITIONS AND METHODS

CROSS REFERENCE TO RELATED APPLICATIONS

This is a §371 U.S. National Phase of International Patent Application No. PCT/US2012/046072, filed Jul. 10, 2012, which claims priority to U.S. Provisional Patent Application No. 61/510,333, filed Jul. 21, 2011, the entirety of which are incorporated herein by reference.

FIELD OF THE INVENTION

This invention relates to compositions and methods for tissue rejuvenation, and more particularly to vaginal tissue rejuvenation.

BACKGROUND

The elastin content of the vagina is decreased in pathological processes such as pelvic organ prolapse, stress urinary incontinence and aging (atrophic) vaginitis. A significant risk factor for the development of these conditions, aside from aging, is trauma to the pelvic floor, most commonly due to a history of vaginal delivery. During labor and delivery the pelvic floor, including the vagina, undergoes significant changes secondary to the mechanical trauma that the tissue endures during delivery. In the post partum period many pelvic floor injuries resolve but frequently symptoms of prolapse and stress urinary incontinence are present in a mild form. As aging occurs the symptoms of prolapse, incontinence and vaginal atrophy become much more bothersome.

The vaginal wall is comprised of three tissue layers the epithelium, the lamina propria, and the muscularis. The vaginal wall contains a significant amount of smooth muscle providing support and structure for the vagina. In addition, these smooth muscle cells are capable of synthesizing components of the extracellular matrix; substances such as elastin through the precursor tropoeleastin and collagen which are responsible for the elasticity and strength of the vaginal wall.

Currently only estrogen is available for the treatment of atrophic vaginitis. However, estrogen has multiple side effects and may lead to the development of cancer or precancerous conditions and for this reason many women are afraid to take it or cannot take it because of a personal history of breast cancer or other estrogen sensitive cancers. No pharmaceutical treatment is currently available for the prevention of stress urinary incontinence or pelvic organ prolapse.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION OF THE INVENTION

The invention provides compositions and methods for inducing the production of elastin and/or collagen in the vagina (e.g., of a human) for the treatment of pathological processes such as pelvic organ prolapse (POP), stress urinary incontinence and aging (atrophic) vaginitis. The invention particularly stimulates such production in the vaginal smooth muscle cells.

Figure 19:
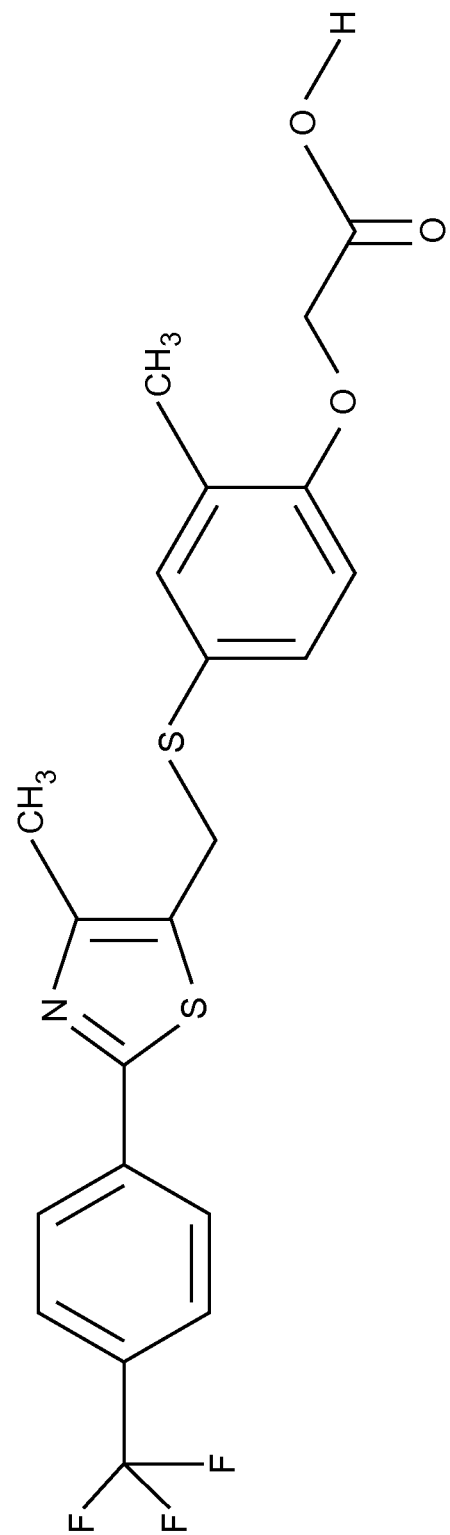
FIG. 19 is a depiction of the chemical structure of GW501516.

GW 501516 (hereinafter sometimes "GW") is a selective peroxisome proliferator-activated receptor beta/delta (PPAR β/δ) agonist that was developed by GlaxoSmithKline (Middlesex, United Kingdom) and is also known by the name GSK-516. This compound is known to activate AMP-activated protein kinase and stimulates glucose uptake in skeletal muscle tissue. The structure of this compound is shown in FIG. 19. The systematic name of the compound is:

2-[2-methyl-4-([4-methyl-2-[4-(trifluoromethyl)phenyl)-1, 3-thiazol-5-yl]methylsulfanyl]phenoxy]acetic acid Other PPAR β/δ modulators could also be useful. Such other PPAR β/δ modulators include, without limitation, GW 0742, tetradecylthioacetic acid, and L-165,041.

The dosage of GW 501516 or other PPAR β/δ agonist can vary. The concentration of GW501516, based on the total weight of the composition, can be 1-50 nM, or between 0-75 nM, or any combination of high and low concentrations within this range such as 1-25, 5-30, and 10-20. The concentration of GW501516, for example, can be 5, 6, 7, 8, 9, 10, 11, 12, 13, 14, 15, 16, 17, 18, 19, 20, 21, 22, 23, 24 or 25 nM. The frequency of administration of the PPAR β/δ agonist compositions can be daily, twice daily, or otherwise as indicated by the patient The amount of the PPAR β/δ agonist formulation that is applied in a single dose can vary.

Formulations including zinc sulfate ($ZnSO_4$) can be utilized. The zinc sulfate can be formulated with one or more carriers. Also, the hydrates of zinc sulfate can be used, such as zinc sulfate heptahydrate. Other water soluble salts of zinc can be used such as, without limitation, zinc acetate, zinc gluconate, zinc chloride, zinc oxide, and zinc lactate.

The dosage of the zinc sulfate can vary. The dosage is selected to provide efficacy without toxicity. The concentration of zinc (as zinc sulfate), for example, can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 μM. The range of concentrations of zinc sulfate can be any high or low concentration of the foregoing, such as 10-30 μM, 15-25 μM, 15-18 μM, or 19-21 μM. The frequency of administration of the zinc compositions of the invention can be daily, twice daily or otherwise as indicated by the patient. The amount of the zinc sulfate formulation that is applied in a single dose can vary.

Compositions including both a PPAR WS modulator such as GW501516 and zinc sulfate can be used. The dosage of GW 501516/zinc sulfate in such combinations can vary. The dosage of the PPAR β/δ modulator such as GW501516 and zinc sulfate, whether used individually or in combination, should be in an amount effective to stimulate production of elastin and/or collagen production in the tissues of the vagina, but not so much as to be toxic to the cells. The concentrations of PPAR β/δ modulators such as GW501516 and zinc sulfate in the combined composition can be as identified above. In one embodiment 20 μM of zinc sulfate is used with 10 nM of GW501516. The frequency of administration of GW 501516/ zinc sulfate in such combinations can be daily, twice daily, or otherwise as indicated by the patient. The amount of the PPAR β/δ agonist/zinc sulfate formulation that is applied in a single dose can vary.

The GW501516 and zinc sulfate can be provided in a number of formulations for topical administration. Suitable delivery modes can include a cream, suppository, ring, pessary, foam, and a tablet. Other delivery modes now in existence or hereafter developed can be utilized. A pharmaceutically acceptable carrier or diluents can be used In one aspect, the pharmaceutically acceptable carrier is polyethylene glycol suppository base.

The compositions and methods of the invention could be used as treatments for the prevention and cure of the following conditions: atrophic vaginitis and related discomfort (vaginal dryness, vaginal and/or vulvar irritation/itching, vaginal soreness, dysuria, and dyspareunia and vaginal bleeding associated with sexual activity), stress urinary incontinence and pelvic organ prolapse (cystocele, rectocele, etc.). The compositions and methods of the invention could be used prior to or after surgery to assist in preventing mesh erosion, or as part of a treatment plan for mesh erosion.

In addition, these treatments may help during the surgical recovery from pelvic organ prolapse or stress incontinence surgery or in the post partum period. The invention would help to rejuvenate the vagina by inducing the production of elastin and/or collagen.

Figure 20:
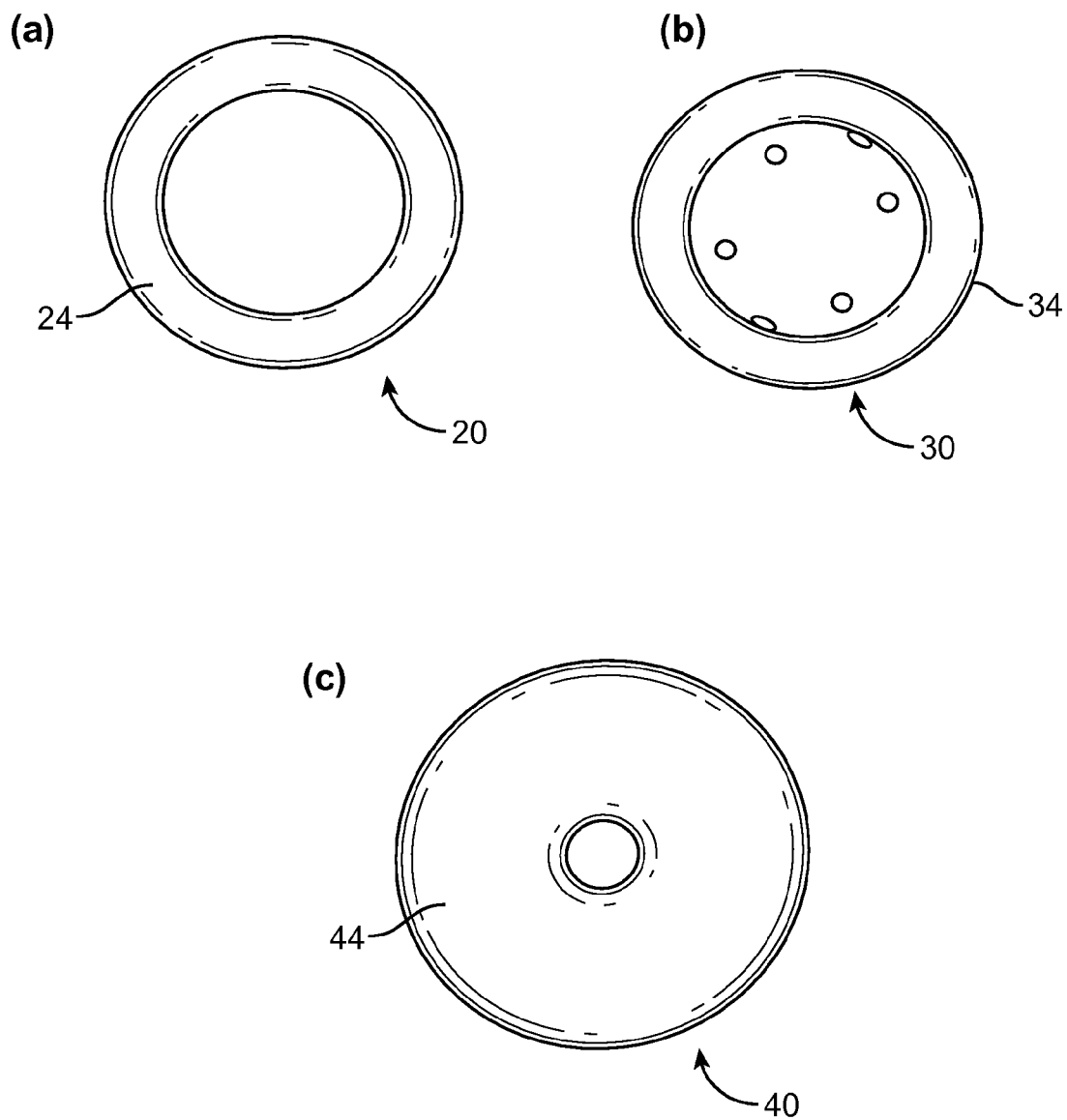
FIG. 20 is a perspective view of (a) ring pessary; (b) ring with support pessary; and (c) doughnut pessary impregnated with compositions according to the invention.

The compositions of the inventions could be provided in a delivery device for controlled release in the vagina. The compositions could be impregnated in a pessary, such that the compositions would provide medication for the condition while the pessary provides structural support. Any pessary suitable for the condition of the patient can be used, such as the ring with support, the ring without support, the doughnut pessary, and others. In FIG. 20 (a) there is shown a ring pessary 20 with an outer circumferential region 24 impregnated with compositions according to the invention. In FIG. 20 (b) there is a ring with support pessary 30 with an outer circumferential region 34 impregnated to deliver compositions according to the invention. In FIG. 20 (c) there is shown a doughnut pessary 40 with an outer circumferential region 44 impregnated with compositions according to the invention. The compositions can be impregnated into or coated onto or otherwise incorporated with the pessary such that the pessary will release the compositions to the tissues of the vagina. Other pessary designs are possible. The pessary will provide mechanical support and also deliver compositions according to the invention, and possibly other compositions, to the site. The compositions of the invention could also possible be incorporated into the mesh for transvaginal mesh procedures as a means to resist mesh erosion.

EXAMPLES

The present invention is further illustrated by the following specific examples. The examples are provided for illustration only and should not be construed as limiting the scope of the invention.

Example 1

Primary Human Vaginal Smooth Muscle Cell Culture Based Experiments

Materials and Methods

Cell cultures of the vagina were produced from women who have undergone a hysterectomy. These cell culture lines were then subjected to different agents to evaluate their effect on elastin production. Zinc sulfate significantly increased vaginal smooth muscle cell elastin production in a dose dependent manner. GW501516 (GlaxoSmithKline) also was noted to significantly increase vaginal smooth muscle cell elastin production. A zinc sulfate and/or selective peroxisome proliferator-activated receptor β/δ agonist containing vaginal cream could be used by women to help to prevent the occurrence, or help relieve their symptoms, of atrophic vaginitis, stress urinary incontinence and pelvic organ prolapse.

Tissue samples of the anterior vaginal wall were obtained from four women without POP undergoing abdominal hysterectomy for benign gynecologic reasons at the University of Miami, Miller School of Medicine, Jackson Memorial Hospital, Miami, Fla. between Dec. 1, 2006 and Dec. 31, 2008. All patients underwent an assessment of POP stages on the basis of the Pelvic Organ Prolapse Quantification System. Women with endometriosis, immunological and connective tissue diseases, recent use of vaginal hormones, and women with prior pessary use were excluded. The site of tissue collection was standardized due to the fact that the vaginal wall composition may vary throughout. After removal of the uterus, full-thickness samples of the anterior vaginal wall were obtained from the vaginal cuff at the anterior midline portion of the vaginal wall, with Metzenbaum scissors. Care was taken to avoid crush injury to the site of the vaginal wall biopsy.

Isolation and Characterization of Vaginal Primary Smooth Muscle Cells

After removal of the uterus, full-thickness samples of the anterior vaginal wall were obtained from the vaginal cuff at the anterior midline portion under sterile condition from four women without POP. Specimens were preserved in cold DMEM/F12 (Invitrogen, Carlsbad, Calif.) supplemented with 10% FBS, 1 mM glutamine, 0.075% $Na_2HCO_3$ and 100 ug/ml penicillin-streptomycin. After a maximum time of 4 hours from tissue harvesting the tissue was mechanically minced in cold cultured media and the fragments were washed 3 times in PBS and were plated onto fibronectin coated plastic dishes (Thermo Fischer Scientific, Rochester, N.Y.). After the initial outgrowth, clones with a morphology resembling the smooth muscle phenotype were patch cloned and propagated in culture. For cell characterization a 5000 cell/well fibronectin coated 8-well chamber slide was plated. Once cell confluence reached 80% the cells were washed twice with PBS and fixed in 4% PFA for 30 min at 37° C. To verify the intracytoplasmic distribution of F-actin fibers 4% PFA fixed cells were exposed to a permeabilizing solution of Tryton X100 0.1% and Rhodamine Phalloidin for 45 min at 37° C. Slides were then treated with mounting media (Vectashield, Vector Laboratories, Burlingame, Calif.) containing DAPI for nucleic acid staining and image acquisition was performed in glycerol immersion by confocal microscopy. In addition, the 8-well chamber slides were used to carry out the immunocytochemical staining. After blockage of endogenous peroxidase activity with a solution of hydrogen peroxide and methanol, slides were sequentially treated with the primary mouse antibody, biotinylated anti-mouse immunoglobulin, and Streptavidin-biotin-peroxidase complex (LSAB™+/HRP kit, Dako, Carpinteria, Calif.). Diaminobenzidine was used as a chromogen in the presence of hydrogen peroxide. Slides were then counterstained with hematoxylin. All reactions were carried out at room temperature (22° C.). To identify the SMC, anti-smooth muscle actin antibodies were used (monoclonal mouse, 1:250, 30 min incubation, clone 1A4, catalog #0851 Dako, Carpinteria, Calif.). Caldesmon expression was studied with a monoclonal mouse antibody, 1:100, 30 min incubation, (clone h-CD catalog #M3557 Dako, Carpinteria, Calif.). An antigen retrieval step was used for caldesmon using citrate buffer and a steamer for 30 min. As a negative control normal mouse serum was substituted for the antibody.

3-[4,5-dimethylthiazol-2-yl]-2,5-diphenyl tetrazoliumbromide (MTT) assay

To perform the MTT proliferation assay, SMC from the fourth to sixth passages (5,000 cells per well) were cultured in 96-well culture plates (Costar, Cambridge, Mass.), in a total volume of 200 µL DMEM/F-12 with 10% FBS. Cells were incubated with zinc sulfate heptahydrate (Sigma, Saint Louis, Mo.) (10 µM, 20 µM and 50 µM), GW501516 (Alexis, Switzerland) (1 nM, 10 nM, 100 nM) in 96-well plates and cell proliferation was assessed by a 3-[4,5-dimethylthiazol-2-yl]-2,5-diphenyl tetrazoliumbromide (MTT) assay at 24 or 48 hrs utilizing a commercially available MTT assay kit (American Type Culture Collection, Catalog #30-1010K, Manassas, Va.). Treatment and control groups were performed in 6 replicate wells. The relative number of viable cells was determined at 24 or 48 hours by incubating the cells with 1 mg/mL of MTT for 4 hours. The live cells utilized MTT resulting in the accumulation of formazan crystals which were then solubilized with acid isopropanol (90% isopropyl alcohol, 2.5% SDS, 0.004 N HCL) for 1 hour. The optical density of the solution was measured at 570 nm.

Fastin Assay for Elastin

SMC from the fourth to sixth passages (5,000 cells per well) were cultured in 96-well or 6-well culture plates (Costar, Cambridge, Mass.), in a total volume of 200 µL or 2 mL DMEM/F-12 with 10% FBS and were grown to near confluence. Cells were incubated with zinc sulfate (10 µM, 20 µM), GW501516 (1 nM, 10 nM, 100 nM) or zinc sulfate with GW 501516 (20 µM with 10 nM) in 96-well plates with serum free DMEM/F-12. Treatment and control groups were performed in 6 replicate wells. Supernatants and cell lysates were collected 24 or 48 hrs after the initiation of treatment. Supernatants and cell lysates were treated with the Fastin Elastin Assay kit (Biocolor Ltd, UK) as recommended by the manufacturer. The Fastin Elastin Assay is a quantitative dye-binding method for the analysis of elastins extracted from biological materials. The dye label employed is 5, 10, 15, 20-tetraphenyl-21, 23-porphine tetra-suffocated (TPPS). The dye reagent binds to the 'basic' and 'non-polar' amino acid sequences found in mammalian elastins. Recovered dye-bound elastin from each sample and standard was read in a 96-well plate at 513 nm. All measurements were performed in quadruplicate. The measured elastin protein amounts were normalized to corresponding cell numbers to provide a reliable basis of comparison between samples.

Sircol Collagen Assay

The Sircol Assay (Biocolor Ltd., UK) is a dye-binding method designed for the analysis of acid and pepsin-soluble collagens. The assay can assess the rate of newly synthesized collagen produced during periods of rapid growth and development. The Sircol Assay is suitable for monitoring collagen produced during in-vitro cell culture and in-vitro extracellular matrix collagens, soluble in cold acid or pepsin, recovered from newly formed extracellular matrix that has been deposited onto cell culture treated plastic surfaces. SMC from the fourth to sixth passages (5,000 cells per well) were cultured in 96-well or 6-well culture plates (Costar, Cambridge, Mass.), in a total volume of 200 µL or 2 mL DMEM/F-12 with 10% FBS and grown up to near confluence. Cells were incubated with zinc sulfate (10 µM, 20 µM), GW501516 (1 nM, 10 nM, 100 nM) or zinc sulfate with GW 501516 (20 µM with 10 nM) in 96-well plates with serum free DMEM/F-12. Treatment and control groups were performed in 6 replicate wells. Supernatants or cell lysate were collected 24 and 48 hrs after the initiation of treatment.

The amount of collagen was determined by SIRCOL collagen assay according to manufacturer's instructions. After removing spent medium, cold acetic acid (0.5M) with pepsin (0.1 mg/ml) was added to the cell culture plates. Extracts were incubated with Sirius red dye and absorbance was determined at 555 nm with a spectrophotometer.

Figure 1:
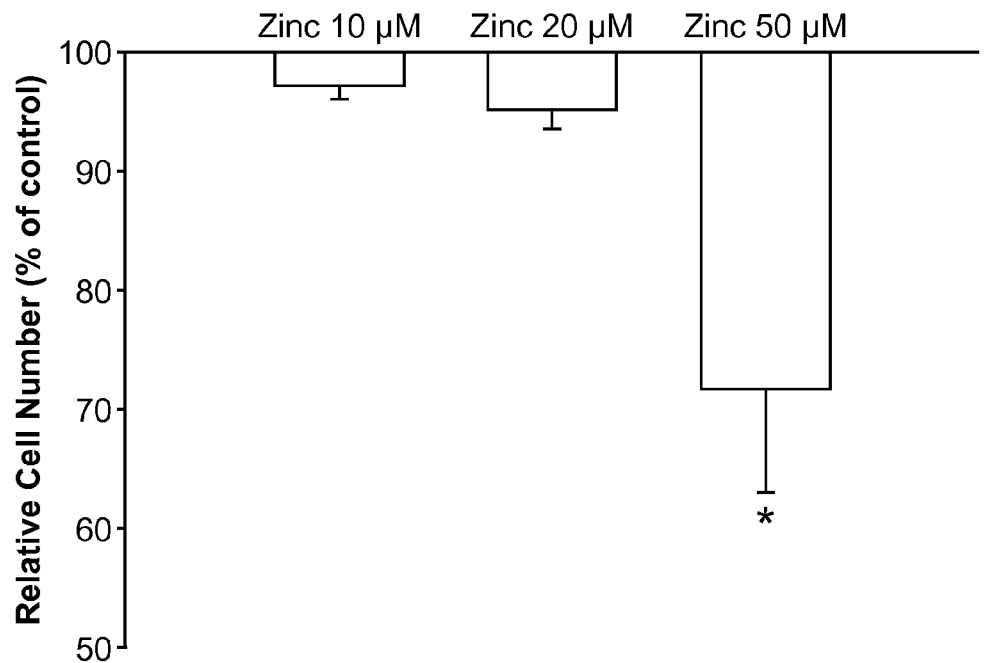
FIG. 1 is a chart illustrating the effect of zinc sulfate on primary vaginal smooth muscle cell proliferation at 48 hrs.

Referring to FIG. 1, SMC (vaginal smooth muscle cells) proliferation was significantly inhibited by 50 µM zinc sulfate (ZS) but not by 10 or 20 µM of ZS compared to the control at 48 hrs of culture [relative cell number (% of control), mean±SD, P-value, control 100, 10 µM (94.7±4.6), NS, 20 µM (90.4±5.5), NS, 50 µM (43.3±30.0), <0.01].

Figure 2:
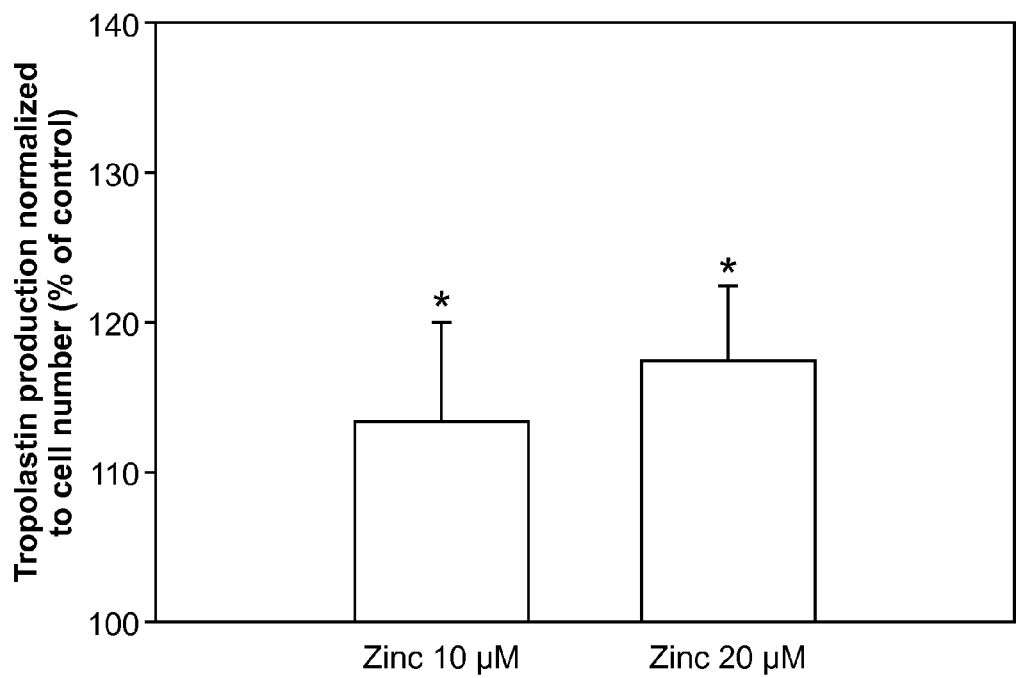
FIG. 2 is a chart illustrating the effect of zinc sulfate on primary vaginal smooth muscle cells tropoelastin production at 48 hrs.

Referring to FIG. 2, SMC tropoelastin production was significantly increased by 10 and 20 µM of ZS compared to the control at 48 hrs of culture [tropoelastin production normalized to cell number (% of control), mean±SD, P-value, control 100, 10 µM (113.3±11), <0.01, 20 µM (117±8.9), <0.01].

Figure 3:
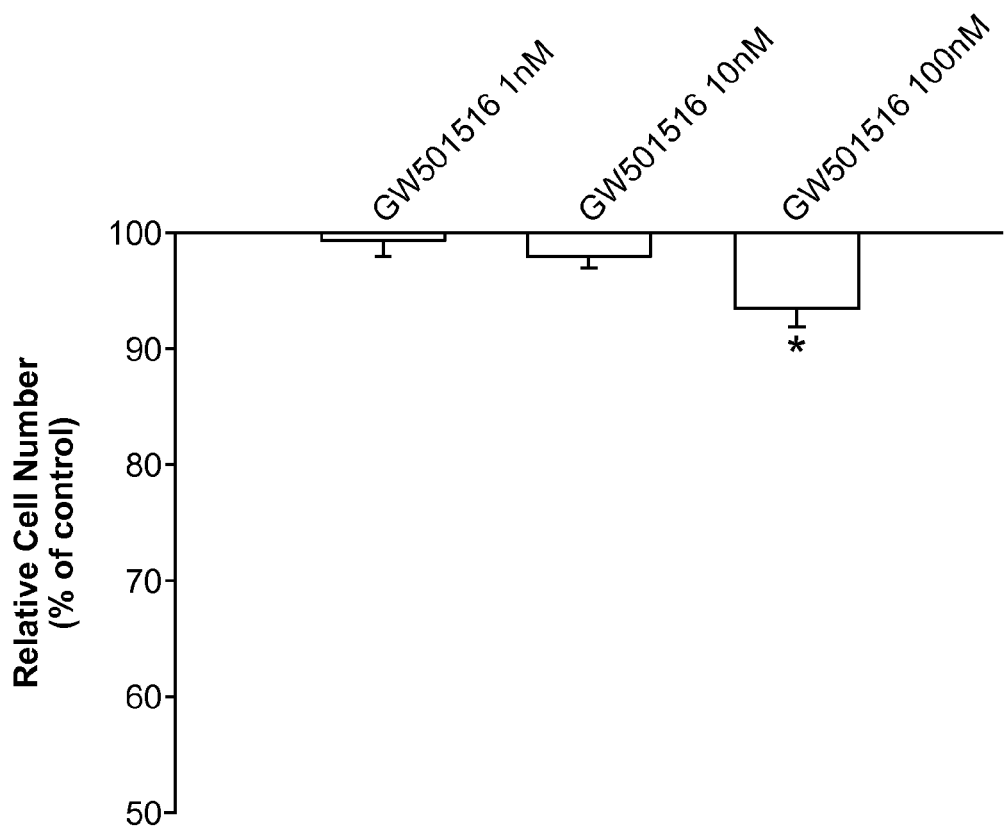
FIG. 3 is a chart illustrating vaginal smooth muscle cells proliferative response to GW501516 at 24 hrs.

Referring to FIG. 3, SMC proliferation was significantly inhibited by 100 nM of GW501516 (GW) but not by 1 or 10 nM of GW compared to the control at 24 hrs of culture [relative cell number (% of control), mean±SD, P-value, control 100, 1 nM (98.9±10.3), NS, 10 nM (95.9±6.5), NS, 100 nM (87.0±10.6), <0.01].

Figure 4:
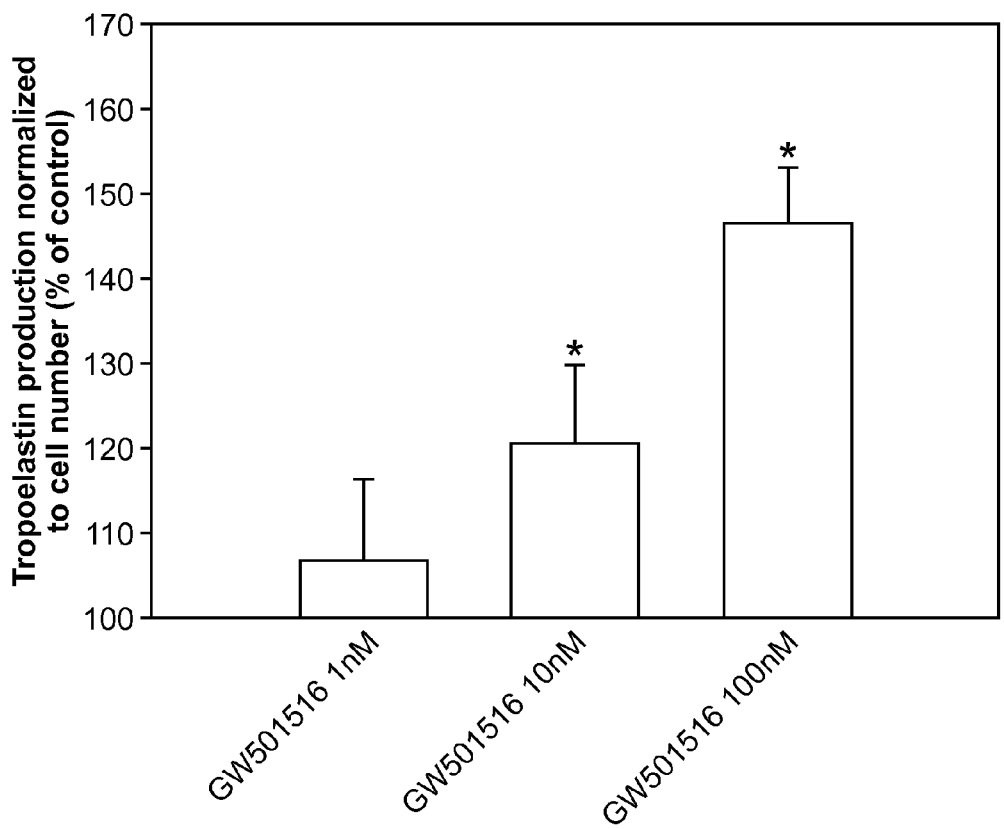
FIG. 4 is a chart illustrating the effect of GW501516 on primary vaginal smooth muscle cells tropoelastin production at 24 hrs.

Referring to FIG. 4, SMC tropoelastin production was significantly increased by 10 and 100 nM of GW501516 compared to the control at 24 hrs of culture [tropoelastin production normalized to cell number (% of control), mean±SD, P-value, control 100, 1 nM (106.6±16), NS, 10 nM (120.5±16), <0.01, 100 nm (146.7±11), <0.01].

Figure 5:
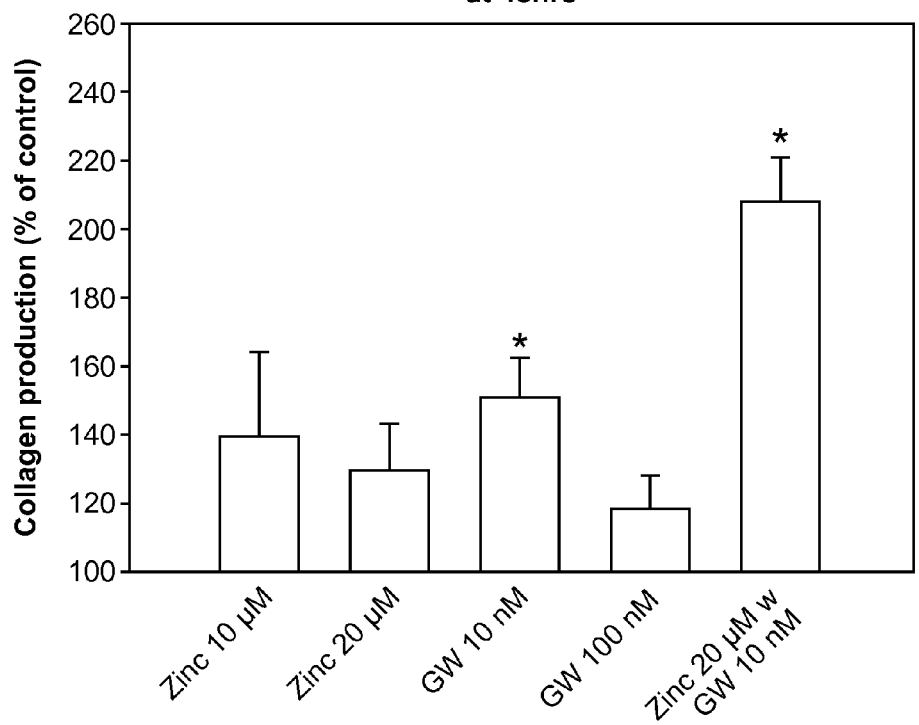
FIG. 5 is a chart illustrating the effect of zinc sulfate and GW501516 on primary vaginal smooth muscle cells cell culture surface deposited collagen production at 48 hrs.

Referring to FIG. 5, cell culture surface deposited collagen production was significantly increased by 10 nM of GW501516 and by the combination of 20 µM of zinc sulfate with 10 nM of GW501516 compared to the control after 48 hours of treatment [collagen production normalized to cell number (% of control), mean±SD, P-value, control 100, zinc sulfate 10 µM (139.3±49), NS, zinc sulfate 20 µM (129.6±27), NS, GW 10 nM (151.0±22), <0.01, 100 nM (118.2±19), NS, zinc sulfate 20 µM with 10 nm GW (208.0±25), <0.01].

Figure 6:
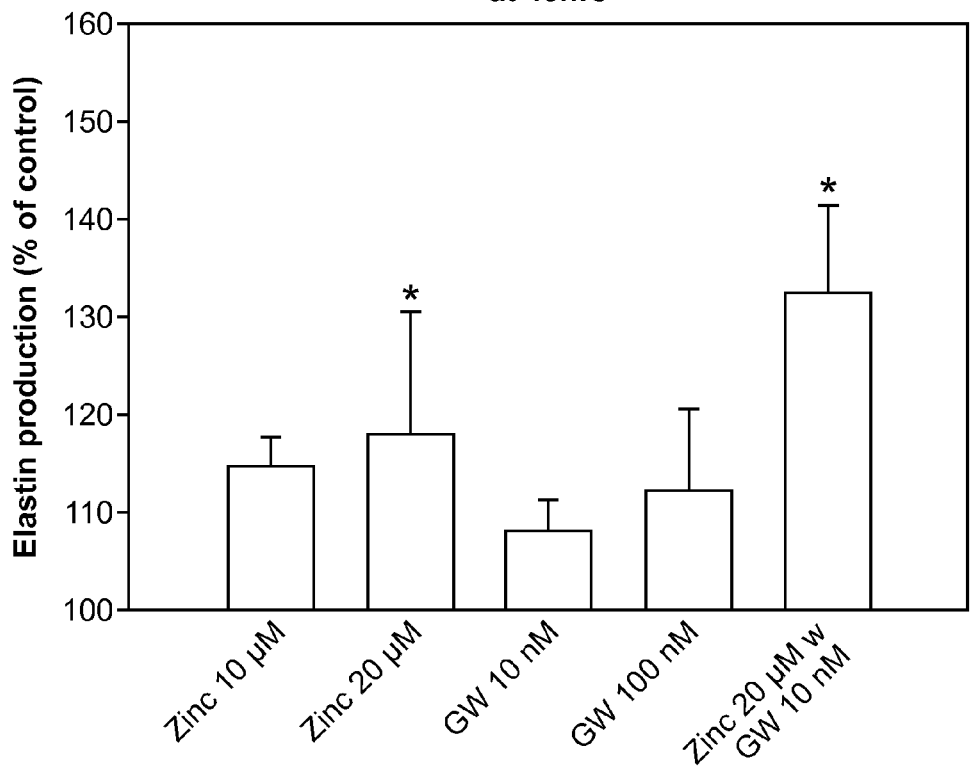
FIG. 6 is a chart illustrating the effect of zinc sulfate and GW501516 on primary vaginal smooth muscle cells cell culture surface deposited elastin production at 48 hrs.

Referring to FIG. 6, cell culture surface deposited elastin production was significantly increased by 20 µM of zinc sulfate and by the combination of 20 µM of zinc sulfate with 10 nM of GW501516 compared to the control after 48 hours of treatment [elastin production normalized to cell number (% of control), mean±SD, P-value, control 100, zinc sulfate 10 µM (114.7±6), NS, zinc sulfate 20 µM (118.0±25), <0.01, GW 10 nM (108.2±6), NS, 100 nM (112.2±16), NS, zinc sulfate 20 µM with 10 nm GW (132.4±17), <0.01].

Example 2

Experiments with Ovariectomized Rats after Treatment for 2 Weeks with Vaginal Suppositories Materials and Methods Ten to 12-weeks old female ovariectomized (OVX) Sprague-Dawley rats were utilized for the experiments. The animals were acclimatized to the environmental conditions before starting the experiment. The animals were housed individually and were allowed free access to water and rodent food. Two weeks after the ovariectomy rats (n=36) were divided into five groups: control (receiving placebo suppositories, n=8), Zinc (receiving zinc sulfate containing suppositories, n=8), GW (receiving GW501516 containing suppositories, n=8), Zinc with GW (receiving Zinc with GW 501516 containing suppositories, n=8) and Estradiol (receiving estradiol containing suppositories, n=4).

Vaginal Suppository Treatment

The suppositories were prepared according to the fusion method, using a polypeg suppository base (MEDISCA, N.Y., USA). The proper amounts of Zinc sulfate heptahydrate (Sigma, Saint Louis, Mo.) or GW 501516 (Alexis, Switzerland) or Estradiol (Sigma, Saint Louis, Mo.) or the combination of Zinc sulfate with GW 501516 were weighted to a final concentration of 20 µM of Zinc sulfate, 10 nM of GW501516, and 0.01% of Estradiol of a total volume of 50±5 µl. Using a microwave, the suppository base was melted in a small beaker for 3 min and then transferred and kept into a water bath at a temperature of 55° C. The proper amount of above reagent was added to the liquefied base and meticulously crushed with a smooth rounded-end glass rod for about 20 min to make the solution to be even and clear. A pipette tip was used to suck some amount of solution and push it into a plastic tube with a diameter of 3.5 mm, and the tube was immediately left on the flat surface of an ice bucket. The suppository turned to white in color when it was solid. The moulded suppository was then pushed out of the tube using a round rod. The moulded suppository was cut using a razor blade to a length of 1.2 cm each, which was calibrated to equal a volume of 50±5 µl per each suppository. After 30 min of cooling at room temperature, the suppositories were stored at 4° C. in a closed chamber until use. They were left to reach room temperature before use.

Macroscopic Measurements and Tissue Collection

The day after the last treatment the rats were overnight fasted and then sacrificed. Macroscopic measurement (genital hiatus, vaginal length) were taken and the vagina was dissected out carefully to avoid any injury to the vagina. The mid section of the vagina was utilized for histology (H and E stain, Masson's trichrome stain) and immunofluorescence and the rest of the vagina was used for RNA extraction and RT-PCR.

Histological Procedures

The mid section of the vagina was fixed in 10% neutral buffered formalin, processed and embedded in paraffin blocks. For each animal, a 4 µm-thick paraffin section was cut and stained with haematoxylineosin and with Masson's trichrome stain for morphological examination. The compactness of the lamina propria collagen fibers were determined semi-quantitatively on a scale from 0-5 (0=loose, 5=tight). The cornification was determined by the presence of a keratin layer on the vaginal epithelium.

Histomorphometry

Measurements of the different vaginal layers were performed on the fifth segment of the vagina, which is approximately halfway between the middle region and the portio vaginalis uteri. This fifth segment was found to display a representative epithelial surface and a sufficient thickness of vaginal smooth muscle layer. Images were captured with a color digital camera and quantified using ImageJ software was used. Using a 10x objective, five measurements per layer per animal were obtained from representative artifact free areas of the epithelium and muscularis, as well as for the three vaginal layers together. The thickness of the lamina propria was obtained by deducting the thickness of the epithelium and muscularis from total vaginal thickness.

Total RNA Isolation and Quantitative Gene Expression Analysis

Total RNA was isolated from 20 mg of vaginal rat tissue in each experimental rat group using the RNeasy Mini kit (Qiagen) according to the manufacturer's specifications. For each total RNA preparation, DNase digestion was performed to remove contaminating genomic DNA. Total RNA samples from each tissue were quantified and evaluated for RNA integrity by the Agilent Bioanalyzer 2100 (Applied Biosystems, Foster City Calif., USA). Following RNA extraction, cDNA was reverse transcribed from ~500 ng of each total RNA preparation using the qScript cDNA synthesis kit (Quanta Biosciences, Gaithersburg Md., USA). Finally, cDNA samples were used to perform gene expression analysis by qRT-PCR using SYBR Green technology on the Real-Plex EP Mastercycler (Eppendorf, Germany) of five genes with known roles in vaginal tissue reconstruction: Collagen IaI (col 1a1), Collagen IIIaI (col 3a1), Collagen VaI (col 5a1), Elastin (eln), Tensin I (tns-1). Glyceraldehyde-3 Phosphate Dehydrogenase (gapdh) was used as a positive control to normalize the expression of each gene. Each qRT-PCR reaction was run in triplicate using Perfecta SYBR Green Supermix (Quanta Biosciences, Gaithersburg Md., USA) in 25 μL reaction volumes using a final concentration of 300 nM forward and reverse primers. For each of the genes analyzed in this study, primers were designed using Primer-BLAST software (NCBI) and synthesized by IDT Technologies (San Diego, Calif.). To minimize the potential for amplification of non-specific transcripts contributed by residual genomic DNA contamination, primers were designed to span at least one intron/exon junction, and forward and reverse primers in each primer set were separated by at least one intron on corresponding genomic DNA sequences. Prior to analysis of experimental samples, RNA extracted from normal rat vaginal tissue was used to validate and optimize each primer set. Standard curves were established to determine the PCR efficiency of each primer set used, gradient PCR reactions were run to establish the optimal annealing temperatures for primer sets in each gene, and melt curves were analyzed to assure specific amplification of desired amplicon targets for each gene. The optimized qRT-PCR reaction run profile for all genes analyzed was determined to be the following: 95° c. for 3 minutes, followed by 40 cycles of 95° c. for 15 seconds, 59° c. for 10 seconds, and 72° c. for 15 seconds. Using the optimized PCR conditions in experimental samples, $C_T$ values for each gene analyzed were first normalized by GAPDH expression, and then relative quantification of gene expression was conducted using the $\Delta\Delta\ C_T$ method. The normalized expression ratios of Col 1a1:Col 3a1 and Col 1a1:Col 5a1 across all experimental animal groups were compared to the untreated animal group.

Immunofluorescence

Samples were incubated with three different antibodies, collagen I, III and anti-actin or collagen I and V and anti-actin. Frozen tissues samples were cut into sections of 6 μm and fixed for 10 min with acetone, followed by five washes of phosphate-buffered saline (PBS). The sections were blocked with 3% goat serum for 30 min, washed five times with PBS and incubated with primary antibodies at room temperature for one hour and washed again five times with PBS. The primary antibody to collagen I is rabbit anticollagen I (1:100) (Abcam, Cambridge, Mass.), collagen III is mouse anticollagen III (1:1000) (Sigma, St Louis, Mo.), and collagen V, is mouse anticollagen V (1:1000) (Chemicon, Billerica, Mass.). After that, sections were incubated with the secondary antibody for one hour in the dark, at room temperature, followed by five washes of PBS. The secondary antibodies for collagen I, III, V and smooth muscle actin are Alexa Fluor 488 Goat Anti-Rabbit IgG(1:500) (Invitrogen, Carlsbad, Calif.); Alexa Fluor 405 Goat Anti-Mouse IgG (1:400) (Invitrogen); Cy3-AffiniPure Goat Anti-Mouse IgM (1:400) (Jackson ImmunoResearch Laboratories, West Grove, Pa.); Alexa Fluor 647 (1;200) phalloidin (Invitrogen). The sections were then mounted with glycerol and a cover slip then dried overnight at 4° in the dark. Four images were obtained per section. Images were capture with an Orca II-ERG 12 bitt CCD camera in a Zeiss Apotome microscope with a 20× objective. The data was analyzed using Matamorph version 7.7.4 software. Results are represented as mean pixel intensity ratios per square area.

Figure 7:
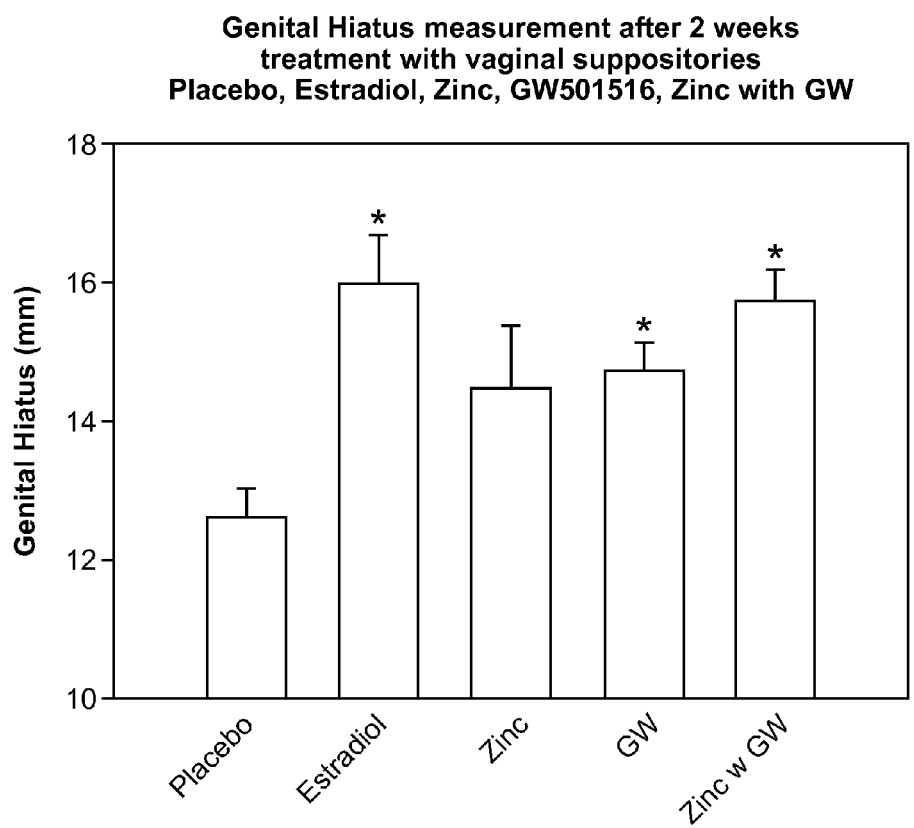
FIG. 7 is a chart illustrating genital hiatus measurement after 2 weeks treatment with vaginal suppositories—placebo, estradiol, zinc, GW501516, and zinc with GW501516.

Referring to FIG. 7, genital hiatus was significantly wider in the animals treated with GW501516, Zinc with GW501516 and estradiol compared to the placebo group [genital hiatus measured in mm (the distance between the external urethral meatus and the mid anus) mean±SD, P-value, placebo 12.6±1.1, Estradiol 16.0±1.4, <0.01, Zinc 14.5±2.5, NS, GW 14.7±1.1, <0.01, Zinc with GW 15.7±1.2, <0.01].

Figure 8:
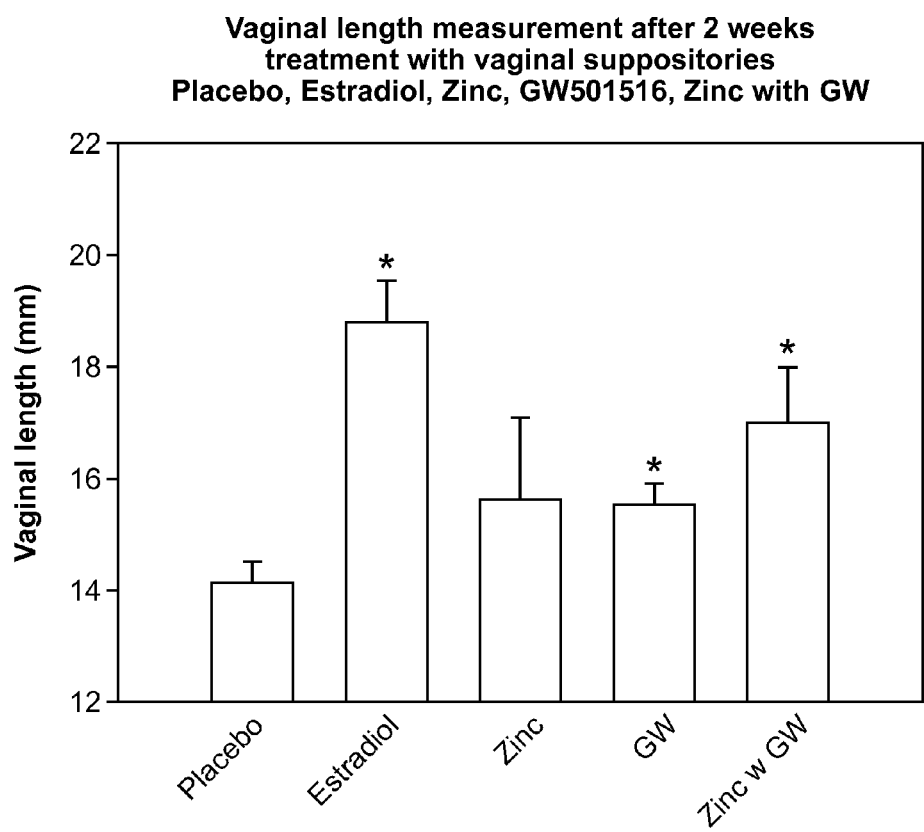
FIG. 8 is a chart illustrating vaginal length measurement after 2 weeks treatment with vaginal suppositories—placebo, estradiol, zinc, GW501516, and zinc with GW501516.

Referring to FIG. 8, the length of the vagina was significantly longer in the animals treated with GW501516, Zinc with GW501516 and estradiol compared to the placebo group [vaginal length in mm, mean±SD, P-value, placebo 14.1±1.1, Estradiol 18.7±1.5, <0.01, Zinc 15.6±4.0, NS, GW 15.5±1.0, 0.02, Zinc with GW 17.7±2.7, 0.01].

Figure 9:
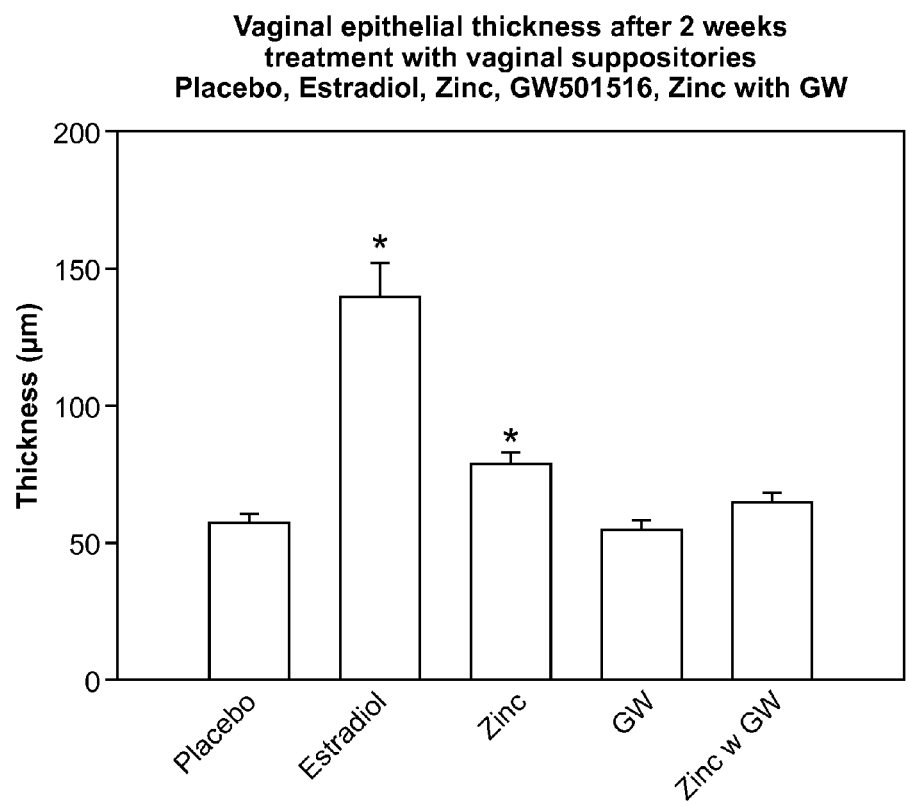
FIG. 9 is a chart illustrating vaginal epithelial thickness after 2 weeks treatment with vaginal suppositories—placebo, estradiol, zinc, GW501516, and zinc with GW501516.

Referring to FIG. 9, the vaginal epithelium was significantly thicker in the animals treated with Zinc and Estradiol compared to the placebo group [epithelial thickness in μm, mean±SD, P-value, placebo 57±18, Estradiol 140±54, <0.01, Zinc 79±21, <0.01, GW 54±23, NS, Zinc with GW 65±20, NS].

Figure 10:
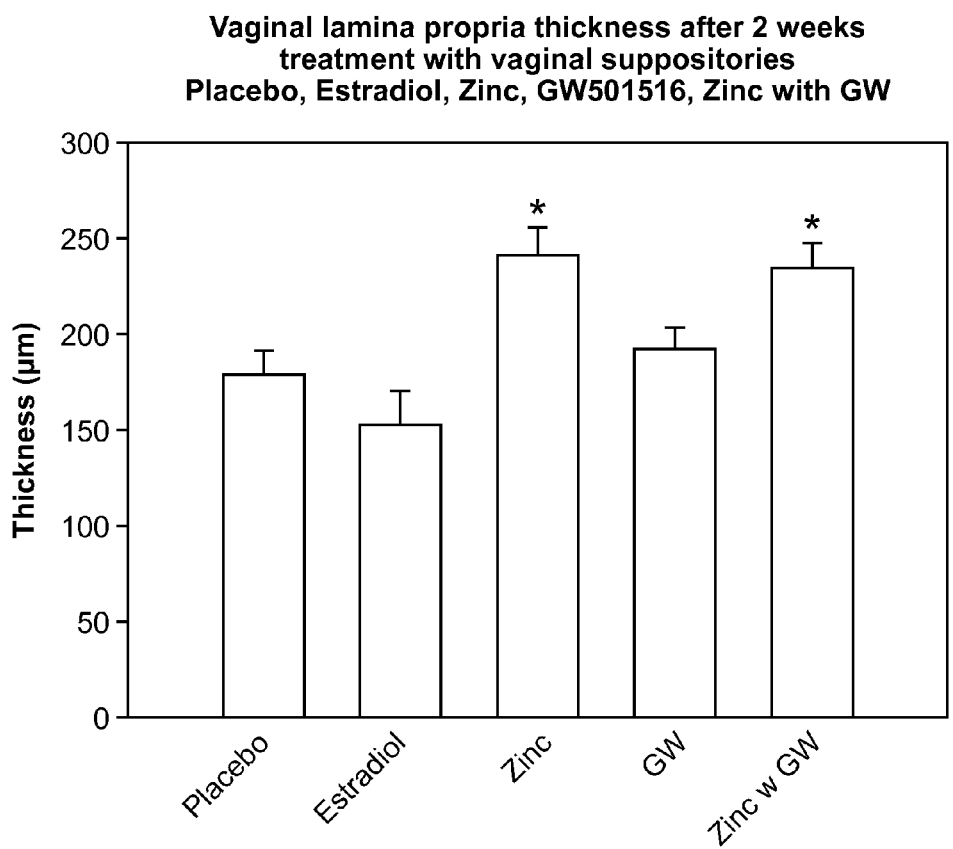
FIG. 10 is a chart illustrating vaginal lamina propria thickness after 2 weeks treatment with vaginal suppositories—placebo, estradiol, zinc, GW501516, and zinc with GW501516.

Referring to FIG. 10, the vaginal lamina propria was significantly thicker in the animals treated with Zinc and Zinc with GW501516 compared to the placebo group [lamina propria thickness in μm, mean±SD, P-value, placebo 179±71, Estradiol 152±80, NS, Zinc 242±78, <0.01, GW 192±68, NS, Zinc with GW 234±80, <0.01].

Figure 11:
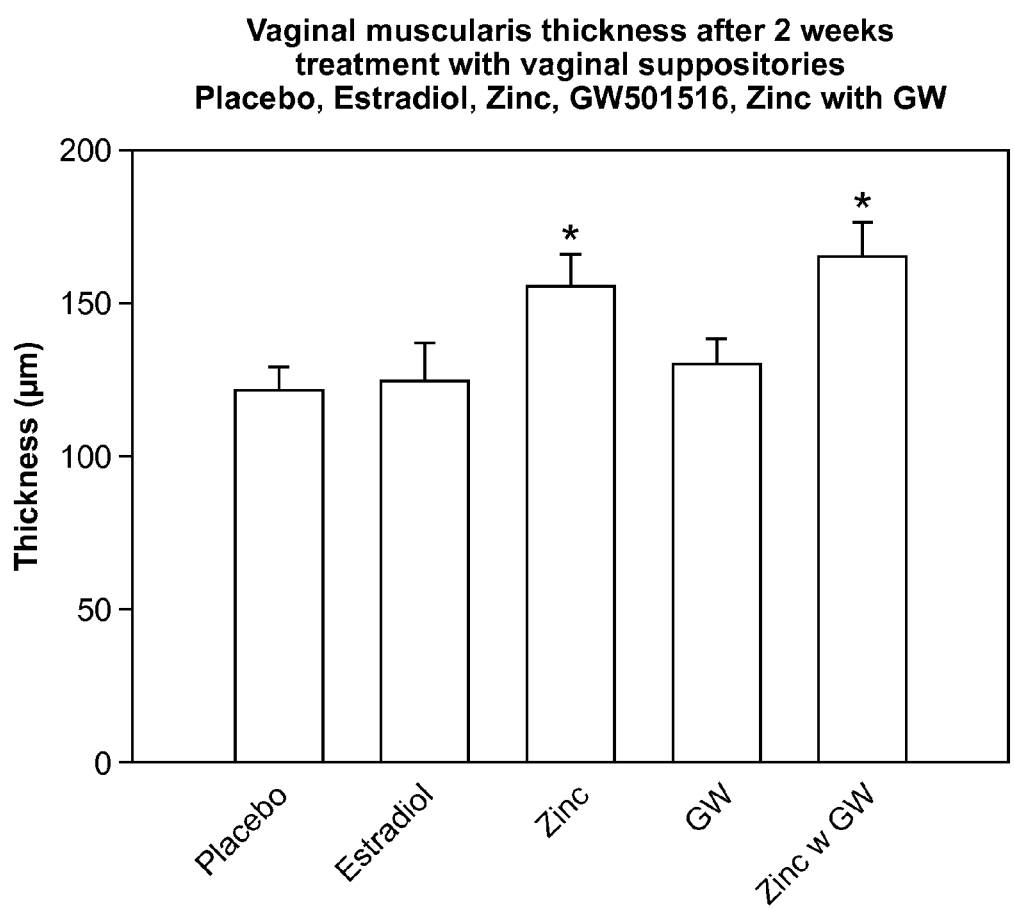
FIG. 11 is a chart illustrating vaginal muscularis thickness after 2 weeks treatment with vaginal suppositories—placebo, estradiol, zinc, GW501516, and zinc with GW501516.

Referring to FIG. 11, the vaginal muscularis layer was significantly thicker in the animals treated with Zinc and Zinc with GW501516 compared to the placebo group [muscularis thickness in μm, mean±SD, P-value, placebo 121±44, Estradiol 124±53, NS, Zinc 155±58, 0.01, GW 130±50, NS, Zinc with GW 165±65, <0.01].

Figure 12:
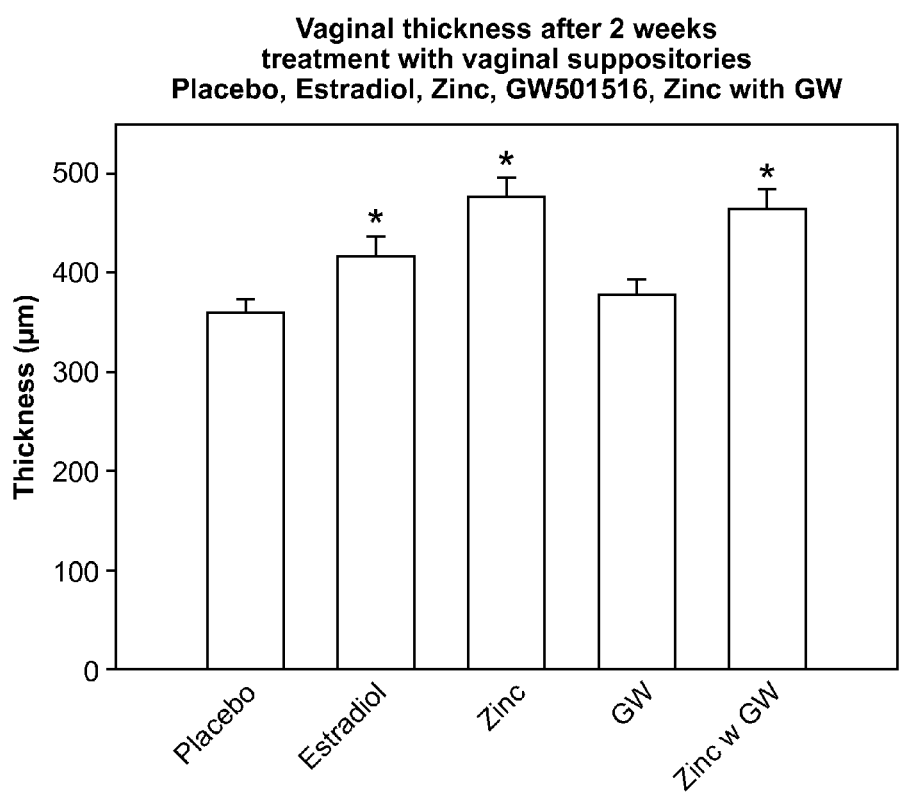
FIG. 12 is a chart illustrating vaginal thickness after 2 weeks treatment with vaginal suppositories—placebo, estradiol, zinc, GW501516, and zinc with GW501516.

Referring to FIG. 12, the vaginal thickness (all three layers of the vagina) was significantly thicker in the animals treated with Zinc, Zinc with GW501516 and Estradiol compared to the placebo group [muscularis thickness in μm, mean±SD, P-value, placebo 358±86, Estradiol 417±82, 0.02, Zinc 477±106, <0.01, GW 377±98, NS, Zinc with GW 464±113, <0.01].

Figure 13:
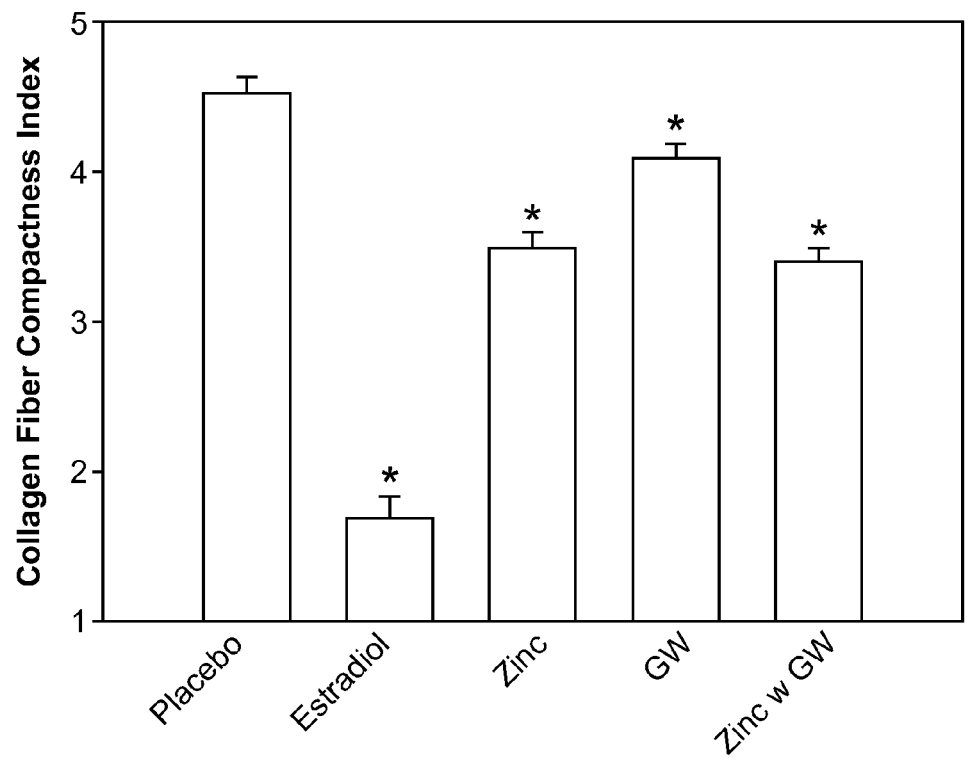
FIG. 13 is a chart illustrating vaginal lamina propria collagen fiber compactness after 2 weeks treatment with vaginal suppositories—placebo, estradiol, zinc, GW501516, and zinc with GW501516.

Referring to FIG. 13, the collagen fiber compactness in the lamina propria layer of the vagina was significantly less dense in the all treatment groups compared to the placebo group [lamina propria collagen fiber compactness, relative units, mean±SD, P-value, placebo 4.5±0.6, Estradiol 1.6±0.6, <0.01, Zinc 3.5±0.5, <0.01, GW 4.0±0.5, NS, Zinc with GW 3.4±0.4, <0.01].

Figure 14:
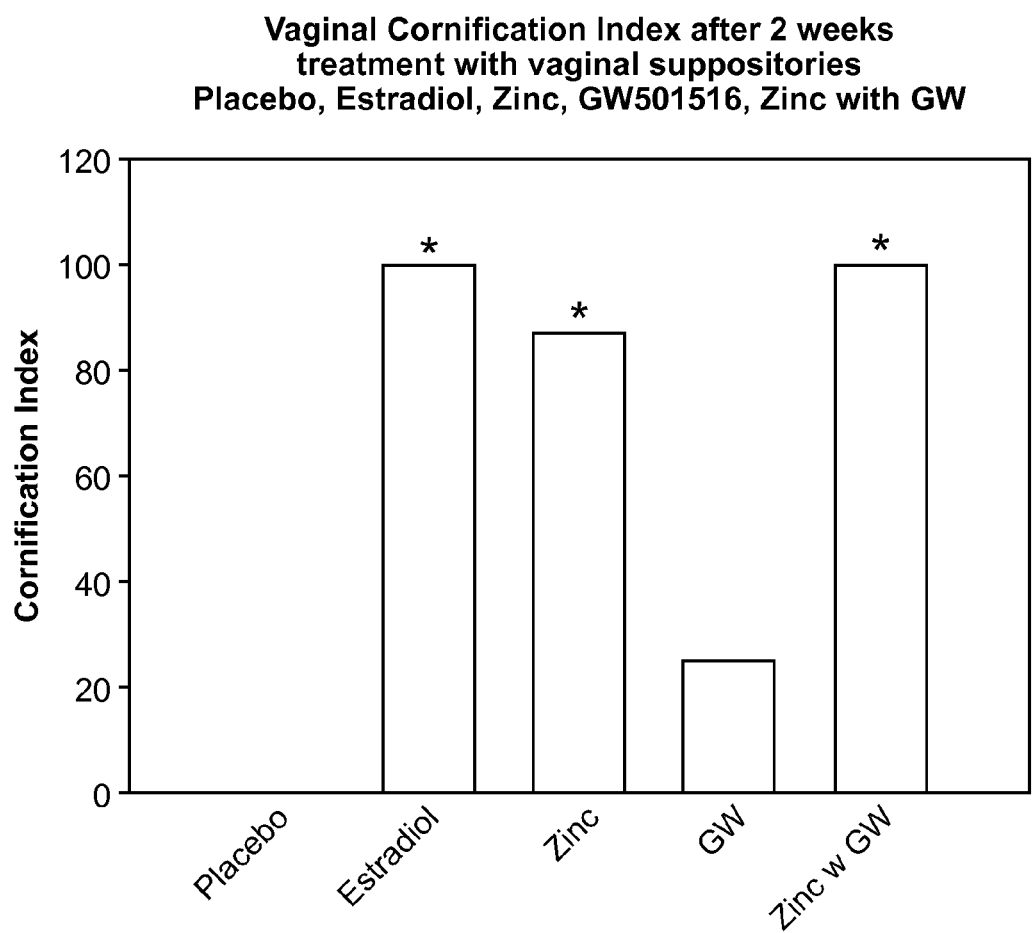
FIG. 14 is a chart illustrating vaginal cornification index after 2 weeks treatment with vaginal suppositories—placebo, estradiol, zinc, GW501516, and zinc with GW501516.

Referring to FIG. 14, the vaginal epithelial cornification rate was 0% in the placebo group, 100% in the Zinc with GW501516 group and the Estradiol group, 87% in the Zinc group and 25% in the GW501516 group.

Figure 15:
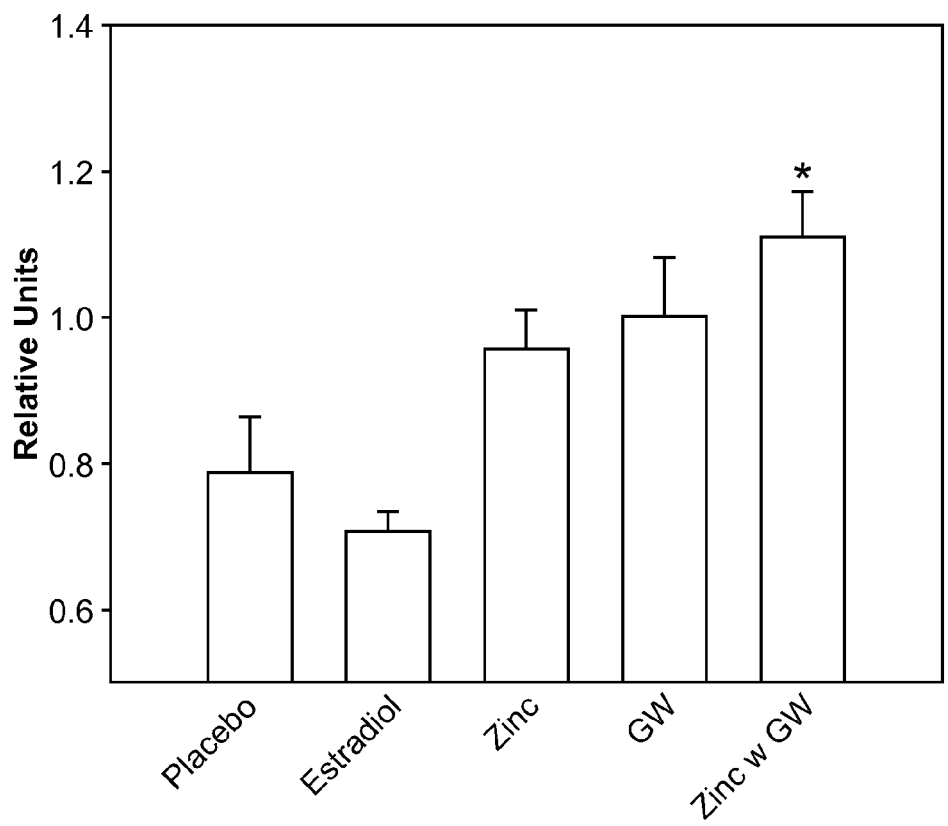
FIG. 15 is a chart illustrating the ratio of rat vaginal Col1a1 mRNA to Col3a1 mRNA expression after 2 weeks treatment with vaginal suppositories—placebo, estradiol, zinc, GW501516, and zinc with GW501516.

Referring to FIG. 15, the ratio of vaginal Col1a1 to Col3a1 mRNA expression was significantly upregulated by Zinc with GW501516 compared to control (placebo group) [relative units, mean±SD, P-value, placebo 0.78±0.2, Estradiol 0.70±0.4, NS, Zinc 0.95±0.1, NS, GW 1.0±0.2, NS, Zinc with GW 1.1±0.1, <0.01].

Figure 16:
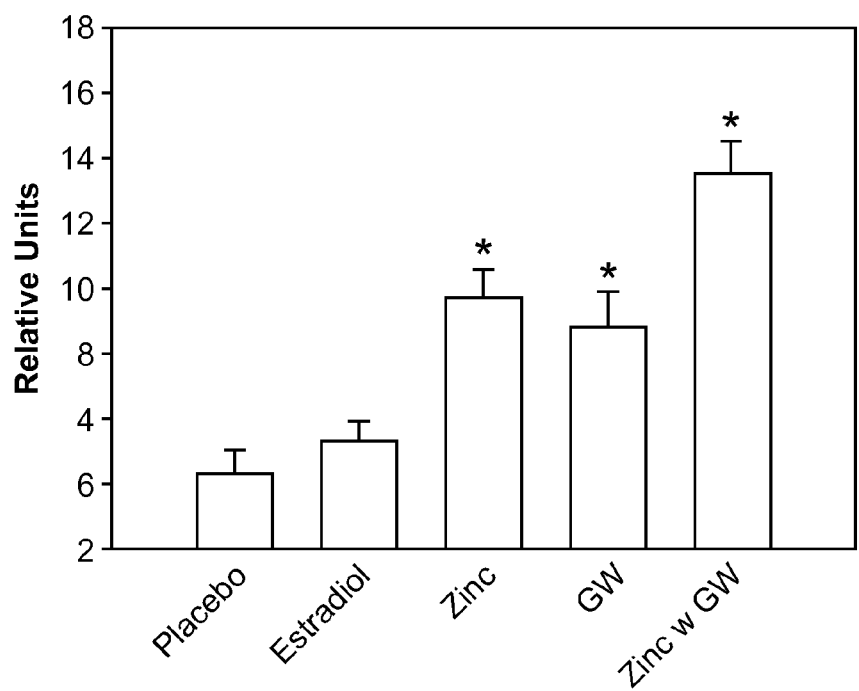
FIG. 16 is a chart illustrating the ratio of rat vaginal Col1a1 mRNA to Col5a1 mRNA expression after 2 weeks treatment with vaginal suppositories—placebo, estradiol, zinc, GW501516, and zinc with GW501516.

Referring to FIG. 16, the ratio of vaginal Col1a1 to Col5a1 mRNA expression was significantly upregulated by Zinc, GW501516 and Zinc with GW501516 compared to control (placebo group) [relative units, mean±SD, P-value, placebo 4.3±1.9, Estradiol 5.3±1.2, NS, Zinc 9.7±2.5, <0.01, GW 8.8±3.0, <0.01, Zinc with GW 13.5±2.7, <0.01].

Figure 17:
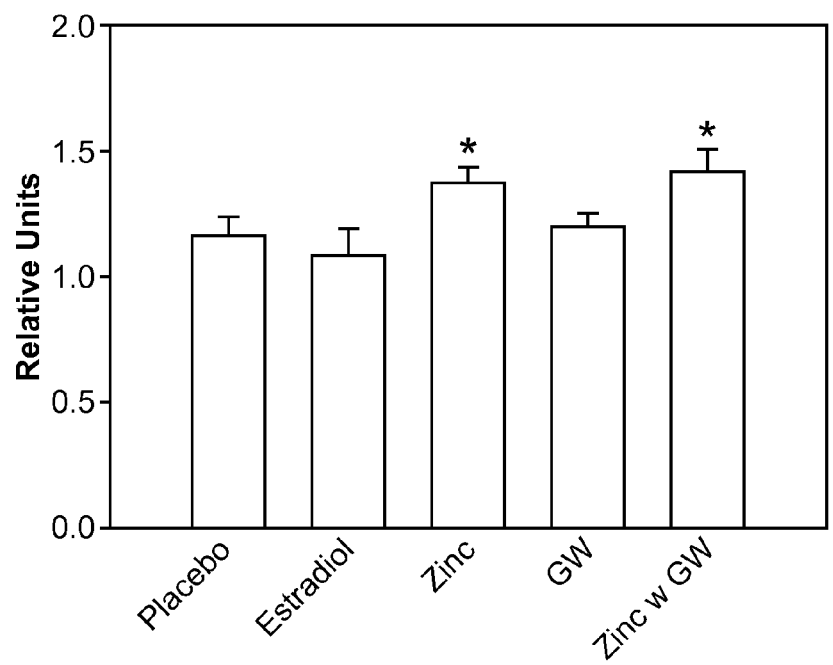
FIG. 17 is a chart illustrating the ratio of rat vaginal Collagen I and Collagen III protein expression after 2 weeks treatment with vaginal suppositories—placebo, estradiol, zinc, GW501516, and zinc with GW501516.

Referring to FIG. 17, the ratio of vaginal Collagen I to Collagen III protein expression was significantly upregulated by Zinc and Zinc with GW501516 compared to control (placebo group) [relative units, mean±SD, P-value, placebo 1.16±0.2, Estradiol 1.08±0.2, NS, Zinc 1.37±0.1, 0.03, GW 1.20±0.1, NS, Zinc with GW 1.41±0.2, 0.03]. The higher the ratio, the healthier the tissue.

Figure 18:
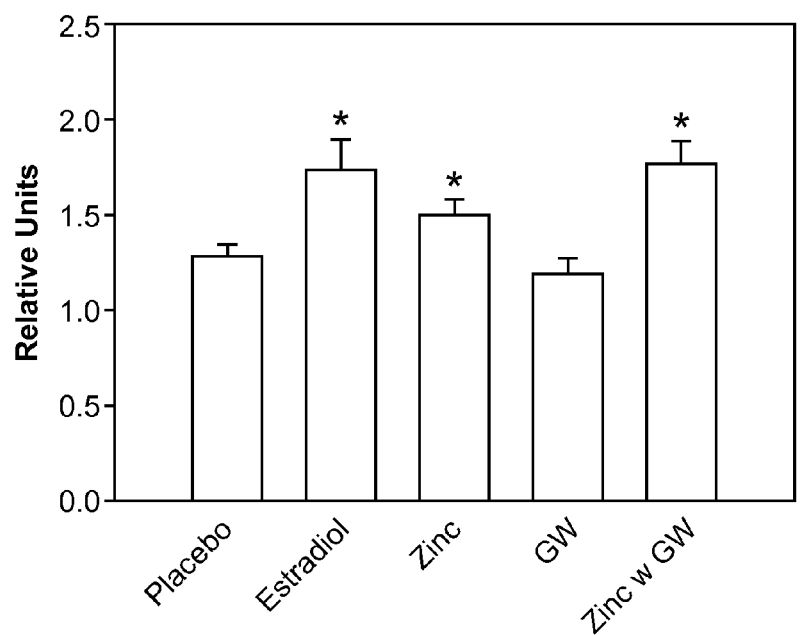
FIG. 18 is a chart illustrating the ratio of ratio of rat vaginal Collagen I and Collagen V protein expression after 2 weeks treatment with vaginal suppositories—placebo, estradiol, zinc, GW501516, and zinc with GW501516.

Referring to FIG. 18, the ratio of vaginal Collagen I to Collagen V protein expression was significantly upregulated by Estradiol, Zinc, and Zinc with GW501516 compared to control (placebo group) [relative units, mean±SD, P-value, placebo 1.28±0.3, Estradiol 1.74±0.5, <0.01, Zinc 1.50±0.4, 0.04, GW 1.20±0.4, NS, Zinc with GW 1.77±0.6, <0.01].

Other Embodiments

Alterations and improvements within the scope of the invention may be made to part or all of the embodiments of The invention as herein described. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

The invention claimed is:

1. A method of stimulating elastin and/or collagen production in the tissues of the vagina of a patient, comprising the steps of:
providing a composition comprising 10-30 μM of a water-soluble zinc salt in an amount effective to stimulate production of elastin and/or collagen in the tissue of the vagina; and
administering the composition to the tissue of the vagina.

2. The method of claim 1, wherein the zinc salt is at least one selected from the group consisting of zinc sulfate, zinc acetate, zinc gluconate, zinc chloride, zinc oxide, and zinc lactate.

3. The method of claim 1, wherein the composition comprises a carrier.

4. The method of claim 1, wherein the composition comprises 10-30 μM zinc sulfate.

5. The method of claim 1, wherein the composition comprises 15-25 μM zinc sulfate.

6. The method of claim 1, wherein the composition comprises 19-21 μM zinc sulfate.

7. The method of claim 1, wherein the zinc salt is zinc sulfate heptahydrate.

8. The method of claim 1, wherein elastin and/or collagen production is stimulated in the smooth muscle cells of the vagina.

9. The method of claim 1, wherein the composition further comprises a peroxisome proliferator-activated receptor beta/delta (PPAR β/δ) agonist.

10. The method of claim 9, wherein the PPAR β/δ agonist is at least one selected from the group consisting of GW501516, GW 0742, tetradecylthioacetic acid, and L-165,041.

11. The method of claim 10, wherein the composition comprises 1-50 nM GW501516.

12. The method of claim 10, wherein the composition comprises 1-25 nM GW501516.

* * * * *